US011672980B1

(12) United States Patent
Tucker et al.

(10) Patent No.: US 11,672,980 B1

(45) Date of Patent: Jun. 13, 2023

(54) METHOD FOR TREATING ANXIETY DISORDERS

(71) Applicant: Brain Electrophysiology Laboratory Company, LLC, Eugene, OR (US)

(72) Inventors: Don M. Tucker, Eugene, OR (US); Phan Luu, Eugene, OR (US)

( * ) Notice: Subject to any disclaimer, the term of this patent is extended or adjusted under 35 U.S.C. 154(b) by 0 days.

(21) Appl. No.: 17/885,639

(22) Filed: Aug. 11, 2022

(51) Int. Cl.
*A61N 1/36* (2006.01)
*A61N 1/04* (2006.01)
*A61B 5/00* (2006.01)

(52) U.S. Cl.
CPC ........ *A61N 1/36025* (2013.01); *A61B 5/4082* (2013.01); *A61B 5/6814* (2013.01); *A61N 1/0484* (2013.01); *A61N 1/36096* (2013.01)

(58) Field of Classification Search
CPC .............. A61N 1/0484; A61N 1/36025; A61N 1/36096; A61B 5/4076; A61B 5/4082; A61B 5/6814
See application file for complete search history.

(56) References Cited

U.S. PATENT DOCUMENTS 7,974,696 B1 * 7/2011 DiLorenzo ........... A61B 5/4082 607/45
10,610,121 B1 4/2020 Tucker
2011/0105998 A1 * 5/2011 Zhang ..................... A61P 21/00 435/375
2012/0289869 A1 * 11/2012 Tyler ........................ A61N 7/00 601/2
2012/0290058 A1 * 11/2012 Langevin .............. A61M 21/02 607/116
2013/0281890 A1 * 10/2013 Mishelevich ...... A61N 1/36085 601/2
2014/0148872 A1 * 5/2014 Goldwasser ....... A61N 1/36034 607/45
2014/0221726 A1 * 8/2014 Pilla ....................... A61N 2/006 600/14
2015/0088224 A1 * 3/2015 Goldwasser ....... A61N 1/36025 607/45
2017/0182285 A1 * 6/2017 Tyler .................... A61B 5/4806
2017/0224990 A1 * 8/2017 Goldwasser ......... A61N 1/0476
2017/0246481 A1 * 8/2017 Mishelevich .......... A61N 2/006
2018/0193641 A1 * 7/2018 Black .................... A61M 21/02
2019/0111258 A1 * 4/2019 Wingeier ............. A61B 5/4064
2019/0232047 A1 * 8/2019 Chu ....................... A61H 23/00
2021/0077771 A1 * 3/2021 Tucker ................. A61N 1/0476

(Continued)

OTHER PUBLICATIONS

Zhao et al., "EEG spectral analysis in insomnia disorder: a systematic review and meta-analysis," Sleep Medicine Reviews 59 (2021).

(Continued)

*Primary Examiner* — Christopher A Flory
(74) *Attorney, Agent, or Firm* — Garth Janke, LLC

(57) ABSTRACT

A method for treating anxiety disorders may include applying a first pair of electrodes on the left side of a subject's head and a second pair of electrodes on the right side of the subject's head; applying a first stimulus carrier of a first magnitude to the first pair of electrodes and a second stimulus carrier of a second magnitude to the second pair of electrodes, wherein the first and second stimulus carriers combine to produce a stimulus having a frequency between 1 Hz and 1 kHz; and steering the stimulus toward the subject's left amygdala.

4 Claims, 5 Drawing Sheets

(56) References Cited

U.S. PATENT DOCUMENTS

| | | | | |
|---|---|---|---|---|
| 2021/0267523 | A1* | 9/2021 | Donoghue | A61N 1/0504 |
| 2021/0361943 | A1* | 11/2021 | Black | A61N 1/0456 |
| 2021/0370064 | A1* | 12/2021 | Murphy | A61B 5/4812 |

OTHER PUBLICATIONS

Luu et al., "Mood, Personality, and Self-Monitoring: Negative Affect and Emotionality in Relation to Frontal Lobe Mechanisms of Error Monitoring," (continued from previous entry) Journal of Experimental Psychology, 2000 vol. 29, No. 1, 43-60.

Tugker et al., "Asymmetric Neural Control Systems in Human Self-Regulation," Psychological Review, 1984, vol. 91, No. 2, 185-215.

Fernandez-Corazza, et al., "Transcranial Electrical Neuromodulation Based Upon the Reciprocity Principle," Frontiers in Psychiatry, Published May 27, 2016.

Kantonen et al., "Interindividual variability and lateralization of mu-opioid receptors in the human brain," NeuroImage 217 (2020).

Lee et al., "Multipair transcranial temporal interference stimulation for improved focalized stimulation of deep brain regions: A stimulation study," (continued from previous entry) Computers in Biology and Medicine 143 (2022).

Luu et al., "Regulating action: alternating activation of midline frontal and motor cortical networks," Clinical Neurophysiology, 112 (2001) 1295-1306.

Tucker and Luu, "Neurophysiology of Motivated Learning: Adaptive Mechanisms Underlying Cognitive Bias in Depression," Cogn Ther Res (2007).

Engel and Fries, "Beta-band oscillations—signalling the status quo?" Current Opinion in Neurobiology 2010, 20:156-165.

* cited by examiner

METHOD FOR TREATING ANXIETY DISORDERS

FIELD OF INVENTION

The present invention relates to the treatment of anxiety disorders, particularly by use of neuromodulation.

BACKGROUND

It is a problem in the treatment of anxiety disorders that the patient's anxiety disrupts the cognitive processing required for effective treatment by use of such techniques as Cognitive Behavioral Therapy. To address this problem, neuromodulation can be used to manipulate brain activity so as to lessen the patient's anxiety during treatment.

Noninvasive neuromodulation, using both Transcranial Magnetic Stimulation (TMS) and transcranial Direct Current Stimulation (tDCS), has been used for the treatment of anxiety. Both forms of electrical or electromagnetic stimulation have been applied to the frontal lobe, with the general rationale that the frontal cortex is the route through which the emotional arousal of anxiety operates to influence the cognition and action of the anxious person.

The present invention takes advantage of a better understanding of what part of the brain should be the target of the stimulation, and how to stimulate that target, for the purpose of treating anxiety disorders.

SUMMARY

Disclosed is a method for treating anxiety disorders. A preferred embodiment of the method includes applying a first pair of electrodes on the left side of a subject's head and a second pair of electrodes on the right side of the subject's head; applying a first stimulus carrier of a first magnitude to the first pair of electrodes and a second stimulus carrier of a second magnitude to the second pair of electrodes, wherein the first and second stimulus carriers combine to produce a stimulus having a frequency between 1 Hz and 1 kHz; and steering the stimulus toward the subject's left amygdala.

Optionally, the step of steering may include varying at least one of the first and second magnitudes so as to produce a varying differential in magnitude therebetween.

Optionally, the step of steering may include contemporaneously obtaining information from the subject regarding the subject's state of anxiety.

Optionally, the method may include identifying a first contiguous subset of the cortex wherein first neurons involved in the pathological beta oscillation are (A) in alignment with each other within a predetermined angular stimulation range; identifying a second contiguous subset of the cortex, distinct from the first contiguous subset of the cortex, wherein second neurons that are also involved in the pathological beta oscillation are both (A) in alignment with each other within the predetermined angular stimulation range, and (B) out of alignment with the first neurons by at least said predetermined angular stimulation range; applying the first stimulus carrier to the first subset of the cortex that is in alignment with the first neurons within said predetermined angular range, and out of phase with the pathological beta oscillation; and applying the second stimulus carrier to the second subset of the cortex that is in alignment with the second neurons within said predetermined angular range, and out of phase with the pathological beta oscillation, wherein the steps of applying the first and second stimulus carriers are sufficient to desynchronize the pathological beta oscillation.

Optionally, the method may include providing a headband structure configured to be worn by the subject, for positioning the electrodes.

It is to be understood that this summary is provided as a means of generally determining what follows in the drawings and detailed description and is not intended to limit the scope of the invention. Objects, features and advantages of the invention will be readily understood upon consideration of the following detailed description taken in conjunction with the accompanying drawings.

DESCRIPTION OF PREFERRED EMBODIMENTS

The present invention provides a method for disrupting pathological neural oscillations related to anxiety disorders, that makes use of what is known in the art of neuroscience as transcranial electrical stimulation ("TES").

The inventor's U.S. Pat. No. 10,610,121 discloses a method for disrupting pathological neural oscillations more generally, which is incorporated by reference herein in its entirety.

Figure 1:
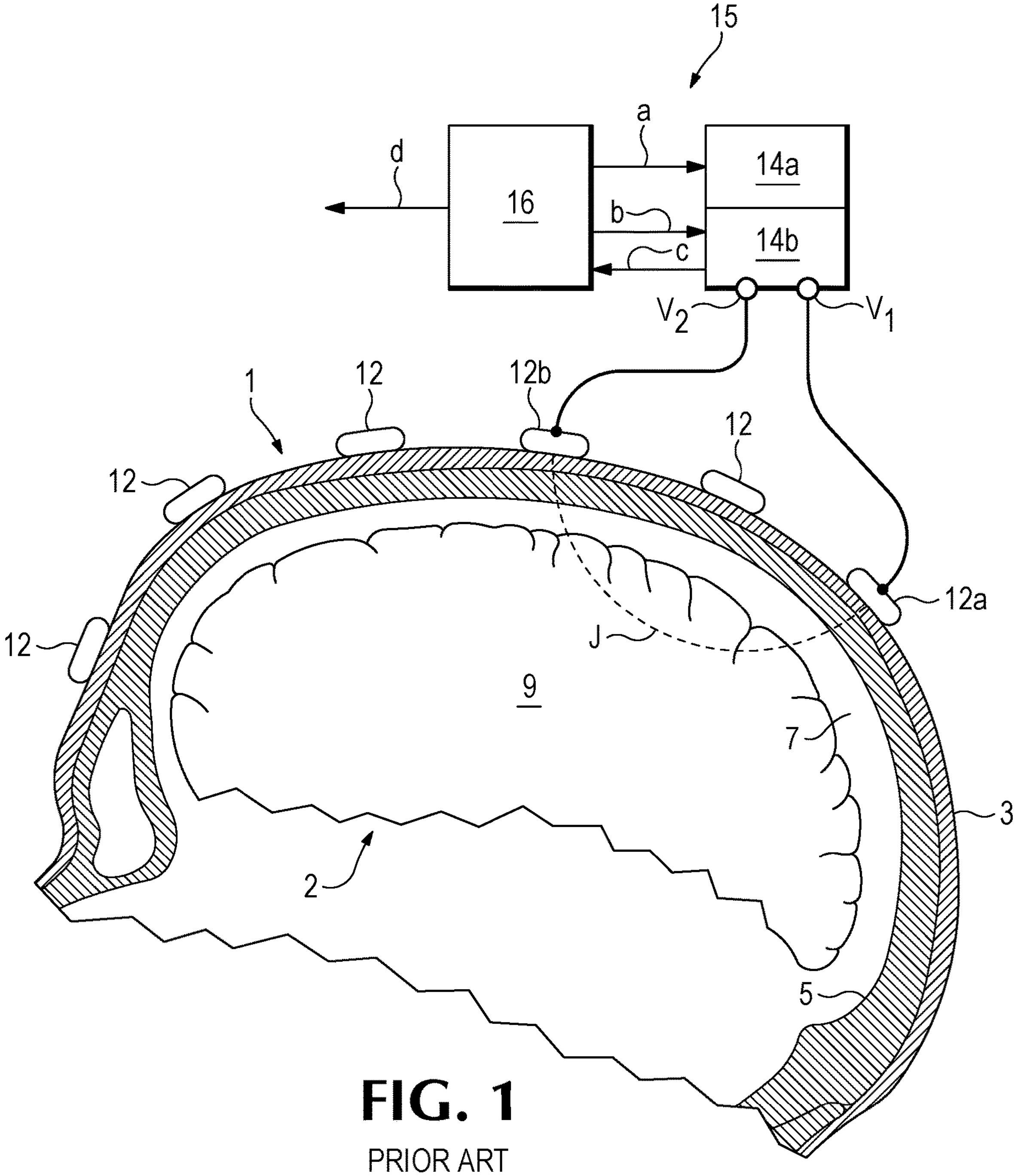
FIG. 1 is a schematic diagram of a system for performing transcranial electrical stimulation of a subject's brain, such as is ordinarily provided in the prior art, and which may be used for practicing methods according to the present invention.

Referring to FIG. 1, TES is well known prior art and need not be discussed in great detail. Basically, it employs electrodes 12 placed in electrical contact with the skin of a subject or patient's scalp, for non-invasively injecting electrical currents into the subject's head 1 for stimulating the subject's brain 2. Specifically, for each of a number of different pairs of scalp electrodes, an electrical current "J" flows from one of the electrodes **12*a* held at a first electrical potential "$V_1$," to another of the electrodes 12*b* held at a second electrical potential "$V_2$," first through the subject's scalp 3, thence through the subject's skull 5, thence through the subject's cerebrospinal fluid 7, and thence through the subject's cortex 9**.

The electrical potentials $V_1$ and $V_2$ may be produced by a system 15 comprising a standard multi-channel voltage source **14*a* (each pair of electrodes defining a channel, the other channels and connections to the electrodes 12 not shown) controlled (arrow "a") by a controller 16** which may be a standard programmable computer such as a PC or Macintosh.

Figure 2:
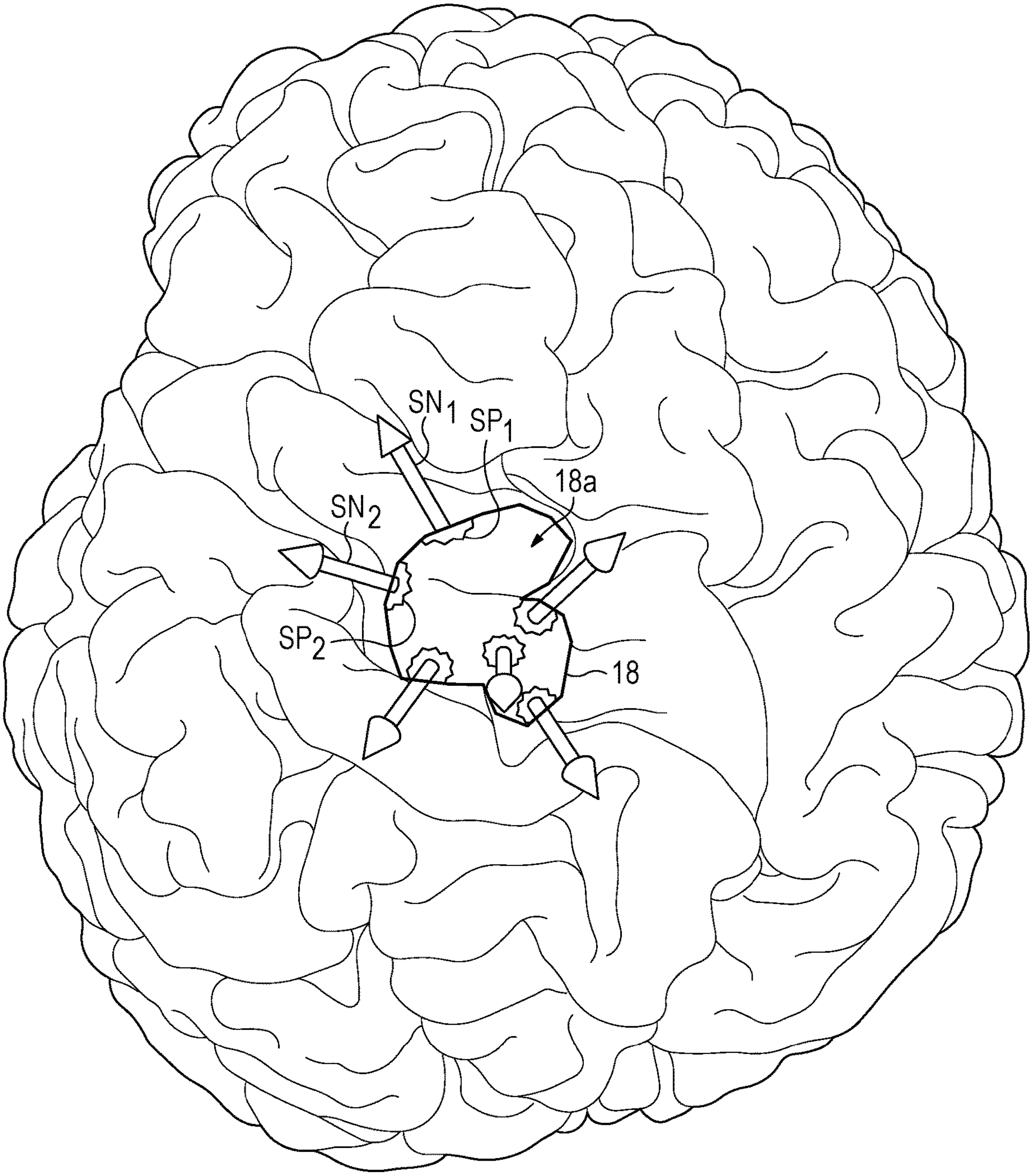
FIG. 2 is an isometric view of a brain, showing a portion of the cortex that is involved in a pathological neural oscillation and identified as a target for stimulation, for desynchronizing the pathological neural oscillation according to the prior art.
Figure 3:
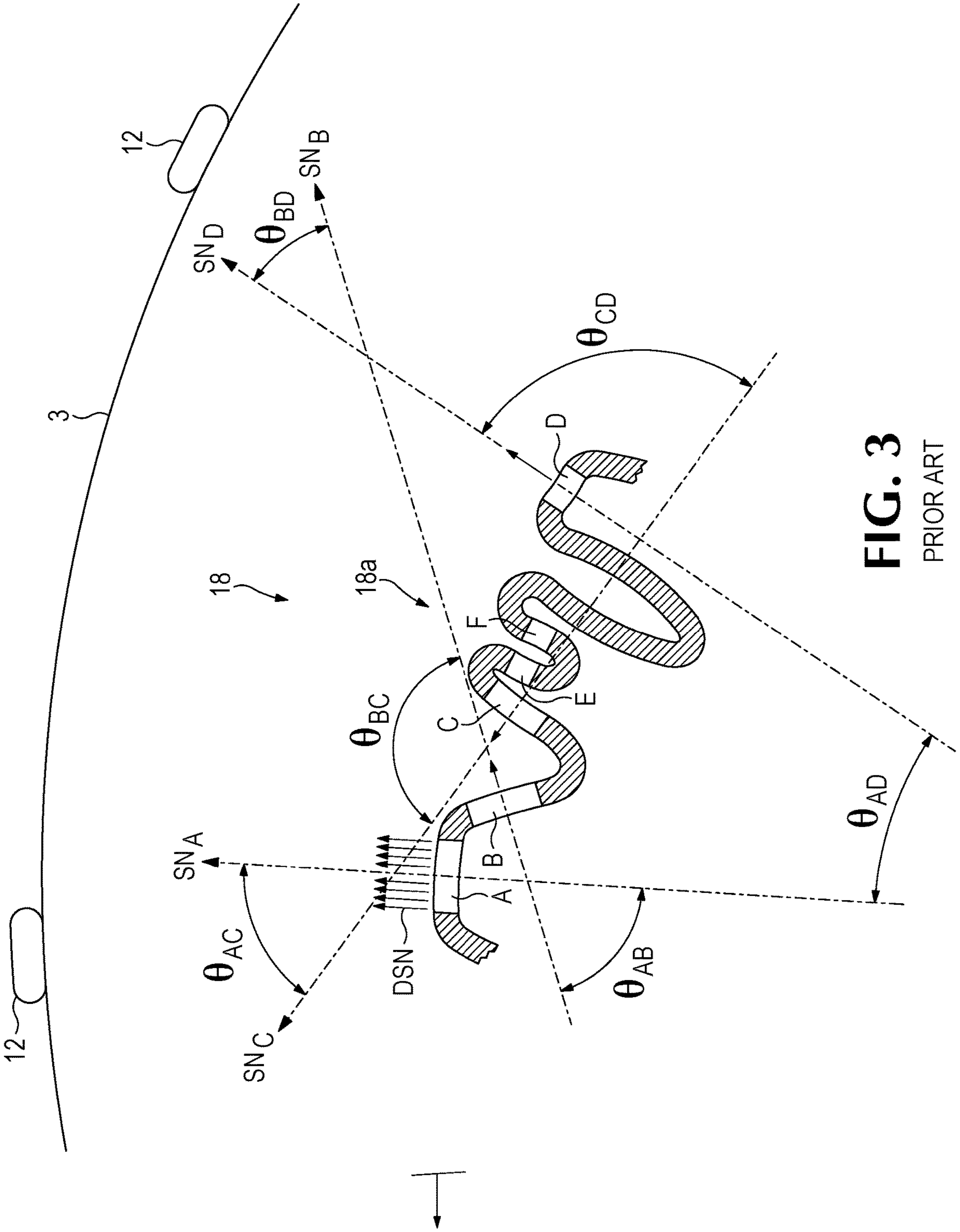
FIG. 3 is a simplified side elevation of the brain of FIG. 2 located beneath the subject's scalp, showing the portion of the cortex in section.

FIGS. 2 and 3 show a portion of the subject's cortex which has been identified as a desired target 18 for desynchronization according to the invention. Such a target may be identified in any manner known in the art, such as from electroencephalographic ("EEG") signatures and/or a priori anatomical knowledge. With particular reference to FIG. 3, for obtaining EEG signatures, the same electrodes 12 that are used for stimulation can be used as sensors of the electrical potentials generated by the brain as is known in the art. In such case, the system 15 would include a standard multi-channel voltage measuring device 14*b*, and the controller 16 may be adapted accordingly for controlling the voltage measuring device to measure electrical potentials (arrow "b") sensed by the electrodes 12, and to send the measured data (arrow "c") to the controller 16, so that the controller 16 may analyze the measured data and/or output the data (arrow "d") for analysis by another device (e.g., a separate computer).

The identified target may further be imaged by any means known in the art, such as by magnetic resonance imaging ("MRI"). The image may be used to conceptually subdivide the target into a number of different subpopulations, such as those referenced as "$SP_1$" and "$SP_2$" in FIG. 2, and "A," "B," "C," and "D" in FIG. 3.

TES does not have a good capability to target specific locations in the brain for stimulation, due primarily to the fact that the stimulating current must pass through bone which is not very conductive. So in general, again referring particularly to FIG. 3, the target 18 would be too small for differential stimulation of the subpopulations A-D were it not for the fact that the cortex is wrinkled. The '121 patent explains that cortical wrinkling allows for differential stimulation of subpopulations using TES, not by targeting specific locations in the cortex, but by targeting specific orientations of the cortical surface; that this type of targeting is based on the fact that any given neuron is most effectively stimulated when the stimulating current is injected normal to the cortical surface where the neuron is located, i.e., parallel to the neuron's dipolar axis; and that the neuron will not as a practical matter be effectively synchronized with an injected stimulating current that deviates from the surface normal by more than a predetermined amount.

The '121 patent defines the maximum angle of misalignment or deviation between the cortical surface normal of a neuron and the direction a stimulating current is injected into the neuron as the "angular stimulation range." The '121 patent explains that, preferably, this range is less than or equal to 45 degrees; more preferably it is less than or equal to 30 degrees, and more preferably it is less than or equal to 20 degrees.

The angular stimulation range can be used for identifying potential subpopulations for selective synchronization or stimulation.

Subpopulations may be identified as being localized groups of neurons within which the surface normal vectors for all the neurons lie inside the angular stimulation range. To provide a simplified illustration of this, FIGS. 2 and 3 show aggregate surface normal vectors that are representative for the subpopulations shown; in FIG. 2, aggregate surface normal vectors "$SN_1$" and "$SN_2$" for the subpopulations $SP_1$ and $SP_2$, and in FIG. 3, aggregate surface normals "$SN_A$" for the subpopulation A, "$SN_B$" for the subpopulation B, "$SN_C$" for the subpopulation C, and "$SN_D$" for the subpopulation D. It is to be understood that, since the cortical surface 18*a* is not planar, the surface normal vectors for each infinitesimal or "differential" portion of the surface of even a relatively small subpopulation will not everywhere be parallel to the aggregate surface normal vectors. With particular reference to FIG. 3, examples of such differential surface normal vectors are shown as "DSN" in connection with the subpopulation A. The aggregate surface normal vectors may be an average, e.g., they may be a mean, median, or integral average, of the differential surface normal vectors DSN.

The '121 patent explains that if all the differential surface normal vectors of a contiguous surface area of the cortex are within the angular stimulation range, that surface area may be considered to define a subpopulation of neurons.

FIG. 3 also illustrates how to distinguish one subpopulation from another according to the invention. It shows aggregate surface normal vectors (again, as illustrative proxies for individual differential surface normal vectors) that make angles with each other that are outside of the angular stimulation range and which are therefore "distinct" from each other. More particularly, the aggregate surface normal vector $SN_A$ for the subpopulation A makes an angle $\theta_{AB}$ with the aggregate surface normal vector $SN_B$ for the subpopulation B, that is outside the preferred 20 degree angular stimulation range. Likewise the angles $\theta_{AC}$, $\theta_{AD}$, $\theta_{BC}$, $\theta_{BD}$, and $\theta_{CD}$, are substantially greater than 20 degrees.

By contrast, the aggregate surface normal vectors (not shown) for the subpopulations labeled "E" and "F" in FIG. 3 are nearly parallel to each other as well as to the aggregate surface normal vector for the subpopulation C, and are therefore well within the angular stimulation range and not distinct from each other. Stimulating any one of these subpopulations will stimulate the other two, and the three subpopulations can be considered for purposes herein as being the same.

The identified subpopulations form a pool, from which at least two subpopulations having distinct differential surface normal vectors may be selected, for selective synchronization with targeted stimulating currents. The stimulating currents are preferably targeted to align with the aggregate surface normal vectors NA for the selected subpopulations.

The source currents used for stimulating the at least two selected subpopulations may be applied over the same periods of time, or during different periods of time, or any desired combination of the two. Moreover, the source current(s) used for stimulating a given selected subpopulation may be applied repetitively, and/or in either a regular or a randomized sequence with the source current(s) used for stimulating the remaining ones of the selected subpopulations.

It has so far been assumed that the pattern and density of the electrodes 12 will allow for differentially stimulating the selected subpopulations, i.e., by injecting one or more currents within the angular stimulation range for a given one of the selected subpopulations, and outside the angular stimulation ranges of the remaining ones of the selected subpopulations. But this may not be the case. The pattern and density of the electrodes will in general be a constraint on the selection of the subpopulations to be stimulated, and may be a constraint on the initial identification of potential subpopulations for stimulation.

To account for this, methods disclosed in the '121 patent may include constructing an electrical head model for the subject, and using the electrical head model to predict current injection paths for different pairings of the electrodes provided in a given pattern and density, to determine pairings of electrodes that can be used to optimally differentially stimulate the greatest number of distinct subpopulations, and/or to optimally define a pattern and density of electrodes to be used. As is typical in the art, the head model may be obtained by combining MRI, X-ray computed tomography ("CT"), and electrical impedance tomography ("EIT") of the subject's head.

All of this disclosure from the '121 patent is being recounted for use in treating anxiety disorders according to the present invention.

It is known that beta oscillations of striatal, limbic, and cortical networks are important to anxiety, and are involved in focusing attention on potential threats. This is normally an adaptive function, as the beta oscillations maintain the "status quo" of ongoing brain network dynamics, and thus maintain the current contents of working memory. But in anxiety disorder, this mechanism becomes exaggerated, leading to a heightened subjective experience of anxiety, and a resulting exaggerated focus on threat that may have pathological emotional and behavioral consequences.

No existing treatment has targeted the beta rhythm of limbic structures specifically, because previous efforts lacked the inventor's new recognition that beta oscillations reflect the focusing of attention under limbic control, particularly for the highly active left amygdalar region.

The present invention also leverages a technique known generally as heterodyning, and which in the context of the present invention employs a pair of relatively high frequency electrical potentials applied across corresponding pairs of electrodes at slightly different frequencies so as to produce, by superposition, a single relatively low frequency electrical potential across both pairs of electrodes at the difference frequency.

The resulting, relatively low frequency electrical potential is for stimulating the brain and may be in the range of 1 Hz to 1 kHz, and will be referred to herein as a "stimulus;" whereas the relatively high frequency electrical potentials should avoid stimulating the brain and therefore should be above about 2 kHz, and will be referred to herein as "carriers" of the stimulus, or "stimulus carriers."

This heterodyning technique allows for propagating electric and/or electromagnetic energy at higher frequencies, so that they encounter less resistance, and so that they are more focused, and therefore provide for better and better focused stimulation of the desired target, i.e., the left amygdalar region. More importantly, the relatively high frequency carrier signals, above 2K Hz or so, pass through brain tissue without affecting neuronal function. In contrast, the low frequency heterodyned or interference signal does affect neuronal function.

Preferably, the relatively high frequency electrical potentials are in phase.

The present invention also leverages a technique known as "steering," where the magnitudes of the relatively high frequencies are varied relative to each other, to help steer the stimulus toward the left amygdalar region.

Methods according to the present invention may also employ feedback from the subject, during the TES procedure, of the subject's subjective experience of anxiety, to help optimize the steering.

Figure 4:
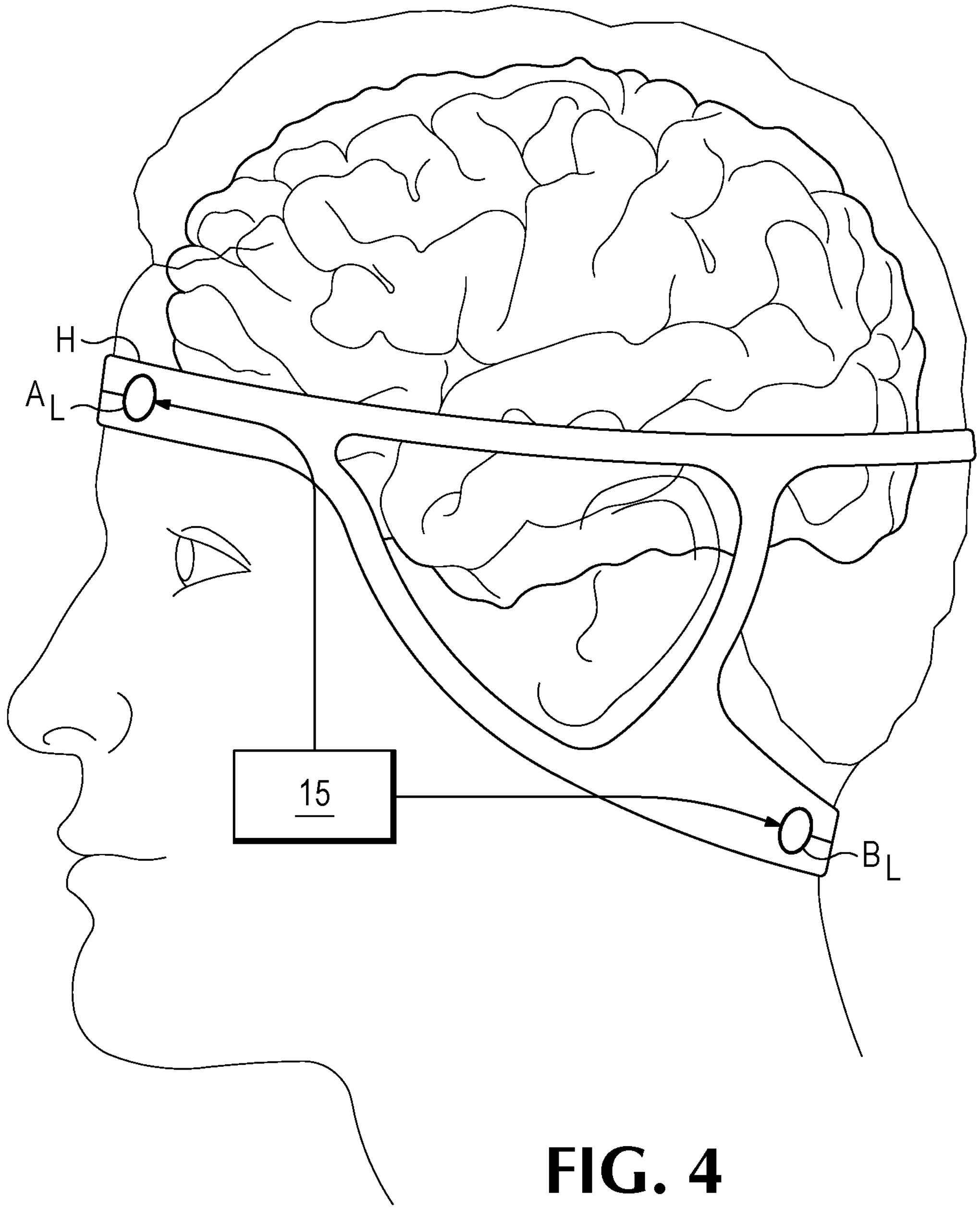
FIG. 4 is left side elevation of the subject's head, showing the left side of a headband structure for positioning electrodes on the left side of the subject's forehead and the left side of the back of the subject's neck, according to the present invention. The drawing is to scale.
Figure 5:
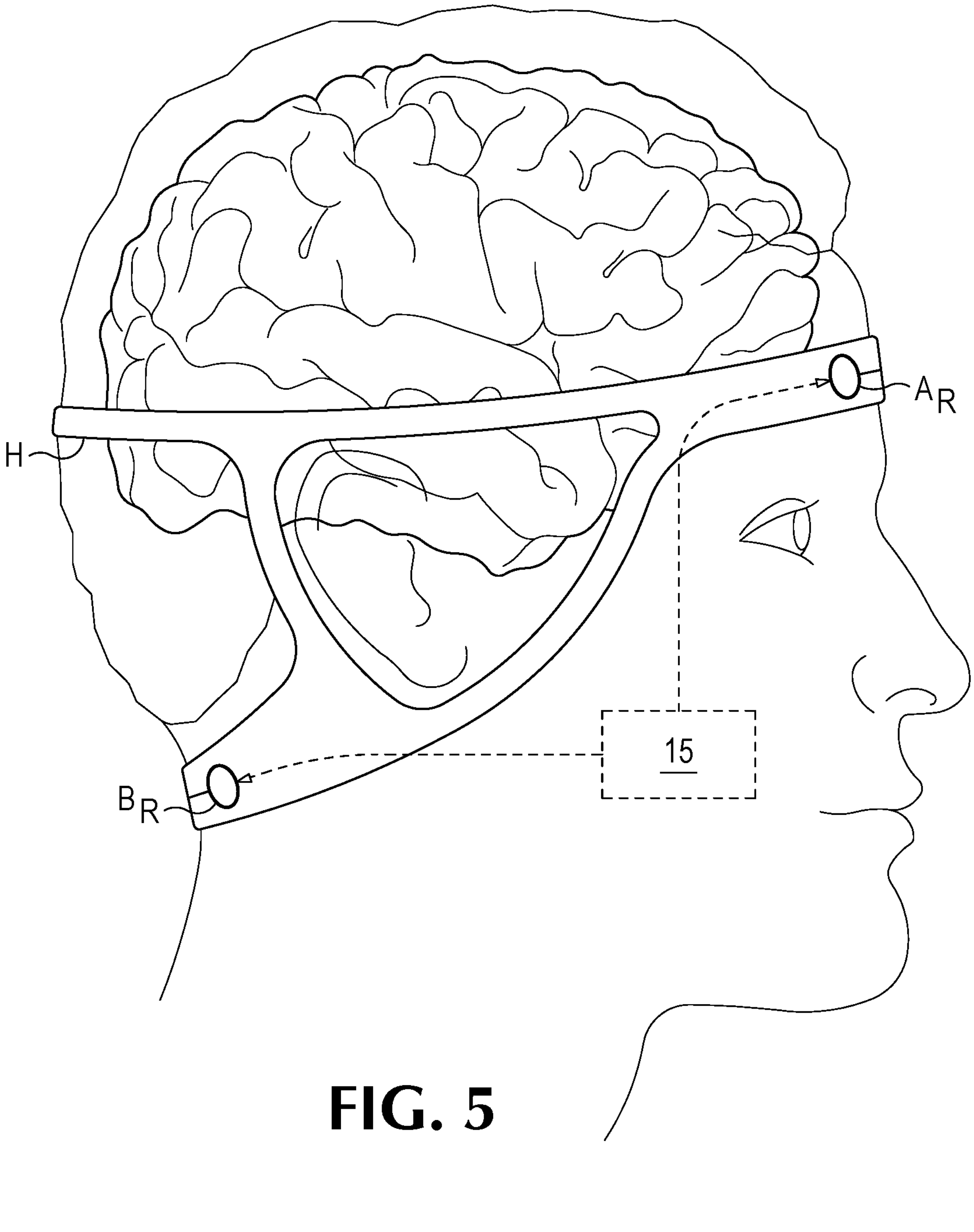
FIG. 5 is a right side elevation of the subject's head, showing the right side of a headband structure for positioning electrodes on the right side of the subject's forehead and the right side of the subject's neck, according to the present invention. The drawing is to scale.

With reference to FIGS. 4 and 5, according to these principles a first relatively high frequency stimulus carrier of a first magnitude may be applied across a first pair of electrodes "$A_L$" and "$B_L$" on the left side of a subject's forehead, and on the left side of the back of the subject's neck, respectively, and a second relatively high frequency stimulus carrier of a second magnitude may be applied across a second pair of electrodes "$A_R$" and "$B_R$" on the right side of the subject's forehead, and on the right side of the back of the subject's neck, respectively, by use of the aforedescribed system 15 shown in FIG. 1.

A suitably configured headband structure "H" such as shown in FIGS. 4 and 5 may be used to position the electrodes.

The heterodyning may be accomplished by providing that the frequency difference between the first and second stimulus carriers is such that the resulting stimulus is in a frequency range between about 1 Hz and 1 kHz. More specifically, for disrupting the targeted beta frequency in anxiety, a stimulus having the typical beta frequency of 14 to 20 Hz, or the person's measured beta frequency, may be used. For example, a first stimulus carrier having a frequency of 10.00 kHz may be combined with or superimposed on a second stimulus carrier having a frequency of 10.017 kHZ to result in a 17 Hz stimulus.

Further according to the invention, the resulting stimulus may be steered toward the subjects left amygdala, such as by varying at least one of the first and second magnitudes so as to produce a varying differential in magnitude therebetween. This results in sweeping the stimulus across the brain, from one hemisphere to the other.

To assist in optimizing the steering according to the invention, the subject may be asked to indicate or report his or her subjective perception or experience of anxiety, or other perception or experience that may be helpful for determining where best to steer the stimulus, during the stimulating procedure.

It is to be understood that, while a specific method for treating anxiety disorders has been shown and described as preferred, other methods could be utilized, in addition to those already mentioned, without departing from the principles of the invention. For example, the same principles described herein can be used for treating comorbidities of anxiety, such as depression and insomnia, and may be used to treat such disorders even if anxiety is not also present.

The terms and expressions which have been employed in the foregoing specification are used therein as terms of description and not of limitation, and there is no intention in the use of such terms and expressions to exclude equivalents of the features shown and described or portions thereof, it being recognized that the scope of the invention is defined and limited only by the claims which follow.

The invention claimed is:

1. A method for treating anxiety in a subject, comprising:

applying a first pair of electrodes on the left side of the subject's head and a second pair of electrodes on the right side of the subject's head;

applying a first stimulus carrier of a first magnitude to the first pair of electrodes and a second stimulus carrier of a second magnitude to the second pair of electrodes, wherein the first and second stimulus carriers combine to produce a stimulus having a frequency between 1 Hz and 1 kHz: and steering the stimulus more toward the subject's left amygdala than the subject's right amygdala: the subject's brain having a cortex and the anxiety being caused by a pathological beta oscillation, the method further comprising identifying a first contiguous subset of the cortex wherein first neurons involved in the pathological beta oscillation are in alignment with each other within a predetermined angular stimulation range, identifying a second contiguous subset of the cortex, distinct from the first contiguous subset of the cortex, wherein second neurons that are also involved in the pathological beta oscillation are both (A) in alignment with each other within the predetermined angular stimulation range, and (B) out of alignment with the first neurons by at least said predetermined angular stimulation range, applying the first stimulus carrier to the first subset of the cortex that is in alignment with the first neurons within said predetermined angular stimulation range, and out of phase with the pathological beta oscillation, and applying the second stimulus carrier to the second subset of the cortex that is in alignment with the second neurons within said predetermined angular simulation range; and out of phase with the pathological beta oscillation, wherein the steps of applying the first and second stimulus carriers are sufficient to desynchronize the pathological beta oscillation.

2. The method of claim 1, wherein said step of steering comprises contemporaneously obtaining information from the subject regarding the subject's state of anxiety.

3. The method of claim 1, wherein said step of steering comprises varying at least one of the first and second magnitudes so as to produce a varying differential in magnitude therebetween, and contemporaneously obtaining information from the subject regarding the subject's state of anxiety.

4. The method of claim 1, wherein said step of steering comprises varying at least one of the first and second magnitudes so as to produce a varying differential in magnitude therebetween.

* * * * *